US006989374B1

(12) United States Patent
Morishita et al.

(10) Patent No.: US 6,989,374 B1
(45) Date of Patent: Jan. 24, 2006

(54) GENE THERAPY FOR CARDIOMYOPATHY

(75) Inventors: Ryuichi Morishita, Osaka (JP); Yoshiaki Taniyama, Osaka (JP); Toshio Ogihara, Osaka (JP)

(73) Assignee: AnGes MG, Inc., Toyonaka (JP)

( * ) Notice: Subject to any disclaimer, the term of this patent is extended or adjusted under 35 U.S.C. 154(b) by 0 days.

(21) Appl. No.: 09/857,719

(22) PCT Filed: Oct. 5, 2000

(86) PCT No.: PCT/JP00/06947

§ 371 (c)(1),
(2), (4) Date: Dec. 3, 2001

(87) PCT Pub. No.: WO01/26694

PCT Pub. Date: Apr. 19, 2001

(30) Foreign Application Priority Data

Oct. 8, 1999 (JP) .................................. 11-288532

(51) Int. Cl.
*A61K 48/00* (2006.01)
*A61K 9/127* (2006.01)
*C12N 15/74* (2006.01)
*C12N 15/11* (2006.01)
*C07H 21/04* (2006.01)

(52) U.S. Cl. ..................... 514/44; 424/450; 435/320.1; 536/23.1

(58) Field of Classification Search ............... 536/23.1; 435/320.1; 514/44; 424/450
See application file for complete search history.

(56) References Cited

U.S. PATENT DOCUMENTS

| 5,652,225 A | 7/1997 | Isner |
| 5,756,122 A | 5/1998 | Thierry et al. |
| 5,792,453 A * | 8/1998 | Hammond et al. ....... 424/93.21 |
| 5,916,193 A * | 6/1999 | Stevens et al. ............. 604/509 |
| 6,248,722 B1 * | 6/2001 | Morishita et al. ............. 514/44 |

FOREIGN PATENT DOCUMENTS

| EP | 0 461 560 A1 | 7/1997 |
| EP | 1142590 | 10/2001 |
| JP | 2777678 | 7/1998 |
| WO | WO 91/06309 | 5/1991 |
| WO | WO 96/40062 | 12/1996 |
| WO | WO97/14307 | 4/1997 |
| WO | WO 97/07824 * | 6/1997 |
| WO | WO99/36103 | 7/1999 |
| WO | WO 01/21214 | 3/2001 |
| WO | WO 01/32220 | 5/2001 |
| WO | WO 03/103721 A1 | 12/2003 |

OTHER PUBLICATIONS

Maurice et al, J Clin Invest Jul. 1999;104:21-9.*
Robbins et al, Pharmcol Ther 1998;80:35-47.*
Miller et al, FASEB J., vol. 9, pp. 190-199.*
Deonarain, 1998, Expert Opin. Ther. Pat., vol. 8, pp. 53-69.*
Kaneda et al, Mol. Med Today 1999;5:298-303.*
Afione, et al., "Gene Therapy Vectors As Drug Delivery System," *Clin. Pharmacokinet.* 29(3):118-89, 1995.
Aoki, et al., "Beneficial Angiogenesis Induced By Over-Expression Of Human Hepatocyte Growth Factor (HGF) In Non-Infarcted And Infarcted Myocardium: Potential Gene Therapy For Myocardial Infarction," *Circulation* 98(17): 1321 (1998).
Ardehali, et al., "Direct Gene Transfer Into Donor Hearts At The Time Of Harvest," J. Thorac. *Cardiovasc. Surg.* 109(4): 716-20 (1995).
Baffour, et al., "Enhanced Angiogenesis And Growth Of Collaterals By In Vivo Administration Of Recombinant Basic Fibroblast Growth Factor In A Rabbit Model Of Acute Lower Limb Ischemia: Dose-Response Effect Of Basis Fibroblast Growth Factor," *Journal of Vascular Surgery* 16(3):181-91 (Aug. 1992).
Brittberg, et al., "Treatment Of Deep Cartilage Defects In The Knee With Autologous Chondrocyte Transplantation:," *The New England Journal of Medicine* 331(14):889-95 (Oct. 6, 1994).
Das, et al., "Molecular Targets Of Gene Therapy," *The Society of Thoracic Surgeons* 68:1929-33 (1999).
Esakof, et al., "Intraoperative Multiplane Transesophageal Echocardiography for Guiding Direct Myocardial Gene Transfer of Vascular Growth Factor in Patients with Refractory Angina Pecoris," *Hum. Gene Ther.* 10(14): 2307-14 (1999).
Folkman, et al., "Angiogenic Factors," *Science* 235:442-47 (Jan. 1987).
French, et al., "Direct In Vivo Gene Transfer Into Porcine Myocardium Using Replication-Deficient Adenoviral Vectors," *Circulation* 90:2414-24 (1994).
Grant, et al., "Scatter Factor Induces Blood Vessel Formation In Vivo," *Proc. Natl. Acad. Sci. USA* 90:1937-41 (1993).
Ishlkawa, et al., "Identification Of Angiogenic Activity And The Cloning And Expression Of Platelet-Derived Endothelial Cell growth Factor," *Nature* 338:557-62 (Apr. 1989).
Isner, et al., "Arterial Gene Therapy For Therapy For Therapeutic Angiogenesis In Patients With Peripheral Artery Disease," *Circulation* 91(11):2687-92 (1995).

(Continued)

*Primary Examiner*—Q. Janice Li
(74) *Attorney, Agent, or Firm*—Klarquist Sparkman, LLP

(57) ABSTRACT

This invention enables the repair of cardiac function by noninvasive administration of an HGF gene in the form of Sendai virus (HVJ)-liposome into the affected cardiac muscle, thereby inducing angiogenesis of the cardiac muscle layer and repressing fibrosis.

4 Claims, 2 Drawing Sheets

OTHER PUBLICATIONS

Lin, et al., "Expression of Recombinant Genes in Myocardium In Vivo After Direct Injection of DNA," *Circulation* 82:2217-21 (1990).

Losordo, et al. "Gene Therapy For Myocardial Angiogenesis," *Circulation* pp. 2800-2804 (1998).

Marshall, Eliot, "Gene Therapy's Growing Pains," *Science* 269:1050-55 (1995).

Miyazawa, et al., "Molecular Cloning And Sequence Analysis Of cDNA For Human Hepatocyte Growth Factor," *Biochemical and Biophyical Research Communications* 163(2):967-73 (1989).

Mulligan, Richard C., "The Basic Science Of Gene Therapy," *Science* 260:926-32 (May 1993).

Nabel, et al. "Recombinant Fibroblast Growth Factor-1 Promotes Intimal Hyperplasia And Angiogenesis In Artieries In Vivo," *Nature* 362:844-46 (Apr. 1993).

Nakamura, et al., "Partial Purification and Characterization of Hepatocyte Growth Factor From Serium of Hepatectomized Rats," *Biochem. Biophys. Res. Commun.*, 122:1450-59 (1983).

Nakamura, et al., "Purification and characterization of a growth factor, from rat platelets for mature parenchymal hepatyocytes in primary cultures," *Proc. Natl. Acad. Sci. USA* 83:6489 (1986).

Nakamura, et al., "Molecular Cloning And Expression Of Human Hepatocyte Growth Factor," *Nature* 342:440-43 (1989).

Pu, et al., "Enhanced Revascularization Of The Ischemic Limb By Angiogenic Therapy," *Circulation* 88(1):208-15 (1993).

Riessen, et al., "Prospects For Site-Specific Delivery Of Pharmacologic And Molecular Therapies," *J. Am. Coll. Cardiol.* 23(5):1234-44 (1994.

Rowland, et al., "Potential Gene Therapy Strategies In The Treatment of Cardiovascular Disease," *Ann. Thorac. Surg.* 60:721-8 (1995).

Rosen, et al., "Scatter Factor (Hepatocyte Growth Factor) is a Potent Angogenesis Factor In Vivo," *Symp. Soc. Exp. Biol.* 47:227-234 (1993).

Schumacher, et al., "Induction Of Neoangiogenesis In Ischemic Myocardium By Human Growth Factors," *Circulation* 97:645-50 (1998).

Seki, et al., "Isolation And Expression Of cDNA For Different Forms Of Hepatocyte Growth Factor From HumanLeukocyte," *Biochemical and Biophyical Research Communications* 172(1)321-27 (1990).

Setoguchi, et al., "Stimulation Of Erythropoiesis By In Vivo Gene Therapy: Physiologic Consequences Of Transfer Of The Human Erythropoietin Gene To Experimental Animals Using An Adenovirus Vector," *The American Society of Hematology* 84(9):2946-53 (1994).

Shi, et al., "Expression Shut Down Following Direct Gene Transfer In The Coronary," *Circulation* 88(4): 2561 (1993).

Simons, et al., "Food For Starving Hearts," *Natural Medicine* 2(5):519-20 (1996).

Stratford-Perricaudet, et al., "Widespread Long-Term Gene Transfer To Mouse Skeletal Muscles And Heart," *J. Clin. Invest.* 90:626-30 (1992).

Takeshita, et al., "Therapeutic Angiogenesis: A single Intraarterial Bolas Of Vascular Endothelial Growth Factor Augments Revascularization In A Rabbit Ischemic Hind Limb Model," *J. Clin. Invest.* 93:622-70 (1994).

Tashiro et al., "Deduced primary structure of rat hepatocyte growth factor and expression of the mRNA in rat tissues," *Proc. Natl. Acad. Sci. USA* 87:3200 (1991).

Ueda, Hideki et al., "In Vivo Gene Transfection Of Hepatocyte Growth Factor Attenuates Ischemia-Reperfusion Injury In The Heart: Evidence For A Role Of HGF In Endogenous Myocardial Protection," *Abstracts From The $70^{th}$ Scientific Sessions* 3459:1-619.

Ueki, et al.,"Hepatocyte Growth Factor Gene Therapy Of Liver Cirrhosis In Rats," *Nature Medicine* 5(2): 226-30 (1999).

Van Belle, et al., "Potentiated Angiogenic Effect of Scatter Factor/Hepatocyte Growth Factor via Induction of Vascular Endothelial Growth Factor," *Circulation* 97(4):381-90 (1998).

Verma, et al., "Gene Therapy—Promises, Problems And Prospects," *Nature* 389:239-42 (1997).

Wakitani, et al, "Repair Of Rabbit Articular Surfaces With Allograft Chondrocytes Embedded In Collagen Gel," *The Journal of Bone and Joint Surgery* 71-B(1):74-80 (1989).

Wechsler, Andrew S., "Molecular Biology 101," *The Society of Thoracic Surgeons* 60:497-98 (1995).

"Antiogenesis Of Patients With Arteriosclerosis," English Translation from the *Japan Finanicial News Paper, Front Page* (Dec. 14, 1998).

"Gene Therapy Taking Into View Recovery of Geriatric Disease," English Translation From The *Japan Financial News Paper. Local News Section* (Dec. 14, 1998).

"Gene Therapy Of Osaka University," English Translation From The *Asahi News Paper* (Nov. 2, 1999).

Nakamura et al., "Purification and subunit of hepatocyte growth factor form rat platelets." *FEBS Letter*, vol. 224, No. 2, pp. 311-316, Nov. 1987.

Takeshita et al., "In Vivo Evidence of Enhanced Angiogenesis Following Direct Arterial Gene Transfer of the Plasmid Encoding Vascular Endothellal Growth Factor" *Circulation*, vol. 88, No. 4, Part 2, pp. 1-476, Abstract No. 2565, Oct. 1993.

"Transgenic Methods in the Gene Therapy for Cardiac Diseases," *Foreign Medical Sciences Section of Pathophysiology and Clinical Medicine*, 19(3), 182-184 (1999).

Sawa et al., "Efficient Gene Transfer Method into the Whole Heart Through the Coronary Artery with Hemagglutinating Virus of Japan Liposome, " *J. Thorac. Cardiovasc. Surg.* 113:512-519 (1997).

\* cited by examiner

GENE THERAPY FOR CARDIOMYOPATHY

CROSS REFERENCE TO RELATED APPLICATIONS

This is the National Stage of International Application No. PCT/JP00/06947, filed Oct. 5, 2000, which claims priority from Japan Patent Application Number 11/288532, filed Oct. 8, 1999.

TECHNICAL FIELD

The present invention relates to a method of gene therapy for treating myocardiopathy by noninvasive administration of an HGF (hepatocyte growth factor) gene and therapeutic agents used therefor. More specifically, the present invention relates to a method of gene therapy for treating myocardiopathy by noninvasive administration of an HGF gene into the cardiac muscle, especially to a method of gene therapy that more efficiently treats heart disease, such as cardiomyopathy, angina pectoris and heart failure, by injecting an HGF gene into the affected part of cardiac muscle under the usage of echo, and to therapeutic agents used therefor. Moreover, the present invention relates to a method of gene therapy which is applicable to genes other than HGF genes and that consists of administering genes to the affected part of tissue noninvasively under the usage of echo.

BACKGROUND ART

In spite of the recent striking technical improvements in the medical field, many problems remain unsolved. The problem of myocardiopathy is one of the important unsolved subjects.

Myocardiopathy is a general name for diseases attributable to organic and functional abnormalities of the cardiac muscle. For example, cardiomyopathy is classified into secondary cardiomyopathy, which occurs in sequence to hypertension, dysbolism, ischemic disease and such, and idiopathic cardiomyopathy (ICM), which occurs without any distinct fundamental disease. Hypertrophic cardiomyopathy (HCM) is classified as an ICM, whose cause of disease is most revealed at the genetic level. In half the numbers of patients which HCM, familial history following autosomal dominant heredity is recognized. Linkage analysis of such family lines, with multiple patients as the object, revealed 5 causal loci so far and the causal gene itself is specified in 4 of them.

Many cases of dilated cardiomyopathy (DCM) occur independently, but familial history is recognized in 20% of the cases. Linkage analysis of such family lines, with multiple patients as the object, revealed 7 types of causal loci (causal genes are unknown).

Regarding myocardiopathy, research is in progress to specify causal gene and to reveal the mechanism underlying the start of disease. So far, no concrete action for gene therapy has been done.

On the other hand, the rapid progress lately in molecular biology has made is possible to activate cellular function by gene transfer methods and various attempts have been made. In particular, there are some reports for gene transfer methods to the heart, like intravenous drip (J.Clin.Invest., 90, 626–630 (1992)), direct injection (Circulation, 82, 2217–2221 (1990); Circulation, 90, 2414–2424 (1994)) or coronary diffusional infusion method that utilizes the plasmid as it is (J.Thorac.Carduivasc.Surg., 109, 716–720 (1995)) and so on, but were far from noninvasive concrete treatment.

DISCLOSURE OF THE INVENTION

The object of this invention is to provide a noninvasive treatment for myocardiopathy, for which effective treatment is currently unknown, and therapeutic agents used therefor. That is, the present invention relates to a method of gene therapy for treating myocardiopathy by noninvasive administration of an HGF gene and therapeutic agents used therefor. More specifically, the present invention relates to a method of gene therapy for treating myocardiopathy by noninvasive administration of an HGF gene into the cardiac muscle, especially to a method of gene therapy for treating myocardiopathy that more efficiently treat a heart disease, such as cardiomyopathy, angina pectoris and heart failure, by injecting an HGF gene to the affected part of cardiac muscle under the usage of echo, and to therapeutic agents used therefor. Moreover, the present invention relates to a method of gene therapy which is applicable to genes other than HGF genes and that consists of administering genes to the part of affected tissue noninvasively under the usage of echo.

Present inventors investigated to find out that effective results are obtained by using an HGF gene as the gene and noninvasively infusing directly to the affected part of cardiac muscle layer. That is, present inventors found out that it is effective to infuse HGF gene to the affected part of cardiac muscle optically using echo without incision of the affected part or thoracotomy. Since this method is a noninvasive treatment, it is possible to administer the present gene repeatedly, according to the condition, and therefore it is possible to treat myocardiopathy efficiently.

Present inventors newly discovered that effective treatments can be done by infusing genes to the affected part optically using echo and showed that the method of the present invention enables genetic treatment of various organ-specific disease.

For example, in the case where the HGF gene is used, according to the present invention, it is possible to treat various organ-specific diseases like pulmonary fibrosis, cirrhosis, hepatic fibrosis and so on. Furthermore, genes other than the HGF gene are also effective in the method of the present invention above.

Thus, the outline of the present invention is as follows:

(1) a therapeutic agent for myocardiopathy used for noninvasive administration comprising a hepatocyte growth factor (HGF) gene as the effective ingredient;

(2) the therapeutic agent of (1), which is used for administration of the HGF gene into the cardiac muscle;

(3) the therapeutic agent of (1) or (2), wherein the HGF gene is in the form of Sendai virus (HVJ)-liposome;

(4) the therapeutic agent of (2) or (3), which is used for noninvasive administration to the affected part of the cardiac muscle under the usage of echo;

(5) the therapeutic agent of any of (1) to (4), which is to be administered at least 8 times, once a week;

(6) the therapeutic agent of any of (1) to (5), wherein at least 10 $\mu$g of the HGF gene is used;

(7) the therapeutic agent of any of (1) to (6), wherein the myocardiopathy is selected from the group consisting of cardiomyopathy, angina pectoris and heart failure;

(8) a gene therapy agent used for noninvasive administration of a gene into an affected part of a tissue under the usage of echo, which comprises genes effective for the treatment of a disorder as the effective ingredient;

(9) the gene therapy agent of (8), wherein the affected part of the tissue is the cardiac muscle;

(10) the gene therapy agent of (8) or (9), wherein the gene is an HGF gene;

(11) a method for gene therapy for myocardiopathy, which comprises the noninvasive administration of an HGF gene into the cardiac muscle of a mammal, including a human;

(12) the method for gene therapy of (11), wherein the HGF gene is in the form of Sendai virus (HVJ)-liposome;

(13) the method for gene therapy of (11) or (12), wherein the HGF gene is administered noninvasively to a part of an affected cardiac muscle under the usage of echo;

(14) the method for gene therapy of any of (11) to (13), wherein the HGF gene is administered at least 8 times, once per week;

(15) the method for gene therapy of any of (11) to (14), wherein the myocardiopathy is selected from the group consisting of cardiomyopathy, angina pectoris and heart failure;

(16) a method for gene therapy, which comprises the noninvasive administration of genes effective for the treatment of a disorder into an affected part of a tissue under the usage of echo;

(17) the method of gene therapy of (16), wherein the affected tissue is the cardiac muscle;

(18) the method for gene therapy of (16) or (17), wherein the gene is an HGF gene;

(19) use of an HGF gene for the production of a therapeutic agent for myocardiopathy used for noninvasive administration;

(20) the use of (19), wherein the HGF gene is in the form of Sendai virus (HVJ)-liposome;

(21) the use of (19) or (20), wherein the therapeutic agent is a therapeutic agent used for the noninvasive administration of the HGF gene to an affected part of the cardiac muscle under the usage of echo;

(22) the use of any of (19) to (21), wherein the myocardiopathy is selected from the group consisting of cardiomyopathy, angina pectoris and heart failure;

(23) use of a gene for the production of a gene therapy agent used for the noninvasive administration of genes effective for the treatment of a disorder into an affected part of a tissue under the usage of echo;

(24) the use of (23), wherein the affected tissue is cardiac muscle; and

(25) the use of (23) or (24), wherein the gene is an HGF gene.

BEST MODE FOR CARRYING OUT THE INVENTION

Figure 1:
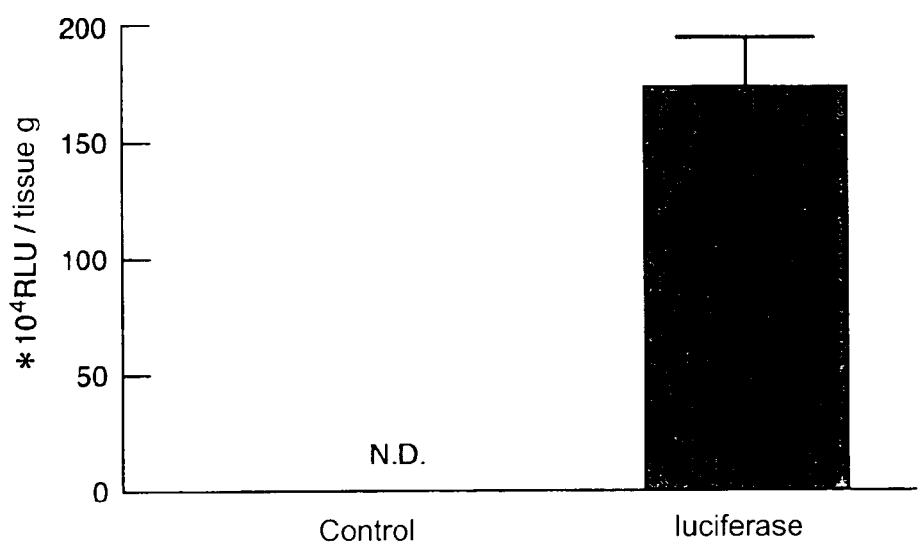
FIG. 1 is a graph showing that gene transfer under usage of echo is possible. It is proven by the high activity rate of luciferase in cardimyopathy guinea pig, in which luciferase as the reporter gene is introduced to the heart using HVJ.

As used herein, "HGF gene" means a gene that can express HGF (the HGF protein). Such genes include genes with deletion of a part of the gene sequence, substitution by another base of the gene sequence, insertion of other base sequence, or binding of bases to the 5' terminus and/or 3' terminus, so long as the expressed polypeptide thereof has substantially the same effect as HGF. For example, HGF genes described in Nature 342:440 (1989); Japanese Patent No., 2777678; Biochem.Biophys.Res.Commun. 163:967(1989); and Biochem.Biophys.Res.Commun. 172: 321(1990) are included. These genes can be used in the present invention.

The base sequence of the HGF gene (the cDNA encoding HGF) of the present invention has been described in the above literature and is also registered with databases, such as Genbank. Thus, based on such sequence information, a suitable DNA portion is used as a PCR primer; for example, by performing an RT-PCR reaction on mRNA derived from the liver or leukocytes, cDNA of HGF can be cloned. Such cloning can easily be performed by a person skilled in the art according to a basic textbook, such as Molecular Cloning 2nd Ed. Cold Spring Harbor Laboratory Press (1989). Modification and such of the HGF gene can be also readily done by a person skilled in the art according to the above basic textbook.

Subsequently, methods of gene transfer, dosage forms, dose and the like for use in gene therapy of the present invention are explained.

The dosage form of a gene therapy agent comprising the above gene as an effective ingredient to be administered to patients are roughly classified into two groups: one is the case in which a nonviral vector is used, and the other is in which a viral vector is used. Methods for preparation and administration thereof are explained in detail in experimental manuals (Supplement of Experimental Medicine, Basic Technology in gene therapy, Yodosha (1996); Supplement of Experimental Medicine, Experimental Methods in Gene Introduction and Expression Analysis, Yodosha (1997); Handbook for Development and Research of Gene Therapy, Japan Society of Gene Therapy ed., NTS (1999)). Specifics are explained below.

A. Usage of a Nonviral Vector

A recombinant expression vector, in which a gene of interest has been integrated into a commonly used gene expression vector, may be used to introduce the gene of interest into cells or tissue by the following method etc.

Illustrative methods of gene transfer into cellsinclude the liopfection method, calcium phosphate co-precipitation method, DEAE-dextran method, direct DNA introduction methods using micro glass tubes, and the like.

Regarding methods of gene transfer into the tissue, the recombinant expression vector may be incorporated into the cell by subjecting it to any method, such as the gene transfer method with internal type liposome, method of gene introduction with electrostatic type liposome. HVJ-liposome method, improved HVJ-liposome method (HVJ-AVE liposome method), receptor-mediated gene introduction method, method of introducing DNA molecules together with carriers (metal particles) by a particle gun, method of directly introducing naked-DNA, method of introduction with positively-charged polymers and the like.

Among them, the HVJ-liposome is a fusion product prepared by enclosing a DNA into a liposome made of lipid bilayer, which is fused to inactivated Sendai virus (Hemagglutinating virus of Japan: HVJ). The HVJ-liposome method is characterized by very high fusing activity with the cell membrane as compared to the conventional liposome method, and is a preferred mode of introduction. For the method of preparing HVJ-liposome, see, the literature for details. (Separate volume of Experimental Medicine, Basic Technology in gene therapy, Yodosha (1996); experimental Methods in Gene Introduction and Expression Analysis, Yodosha (1997); J.Clin.Invest. 93:1458–1464 (1994); Am.J-.Physiol. 271:R1212–1220 (1996)) and the like, and experimental examples described below for details.

In particular, the Z strain (available from ATCC) is preferred as the HVJ strain, but other HVJ strains (for example, ATCC VR-907 and ATCC VR-105) may also be used.

Furthermore, the method of directly introducing naked-DNA is the most simple method among the methods describer above, and in this regard a preferred method of introduction.

Expression vectors as used herein may be any expression vectors so long as they permit the in vivo expression of the gene of interest. Examples include expression vectors such as pCAGGS (Gene 108:193–200 (1991)), pBK-CMV, pcDNA3.1, pZeoSV (Invitrogen, Stratagene) and the like.

B. Usage of a Viral Vector

Representative methods that use viral vectors include those using viral vectors such as recombinant adenovirus, retrovirus and the like. More specifically, the gene of interest can be introduced into a DNA or RNA virus such as detoxified retrovirus, adenovirus, adeno-associated virus, herpes virus, vaccinia virus, poxvirus, poliovirus, Sindbis virus, Sendai virus, SV40, human immunodeficiency virus (HIV) and the like, which is then infected to the cell to introduce the gene into the cell.

Among the above viral vectors, the efficiency of infection of adenovirus is known to be much higher than that of other viral vectors. In this regard, it is preferred to use an adenovirus vector system.

As methods of introducing a gene therapy agent into a patient, there are in vivo methods, which permit direct introduction of the gene therapy agent into the body, and ex vivo methods, in which certain cells are removed from human, to which the gene therapy agent is introduced and which are returned into the body thereafter (Nikkei Science, April 1994 issue pp. 20–24; Monthly Yakuji, 36(1): 23–48 (1994); Supplement To Experimental Medicine 12 (15) (1994); Handbook for Development and Research of Gene Therapy, NTS (1999)). According to the present invention, the in vivo method is preferred.

Dosage forms may take various forms according to various administration regimens described above (for example, liquids). When, for example, an injection containing the gene as an effective ingredient is to be used, said injection may be prepared by dissolving the effective ingredient(s) into a standard solvent (a buffer such as PBS, physiological saline, sterile water, etc.). The injection liquid may then be filter-sterilized with filter as needed and then filled into sterilized containers. Conventional carriers and so on may be added to the injection. Liposomes, such as HVJ-liposome, may take the form of suspensions, frozen formulations, centrifugation-concentrated frozen formulations, and the like.

In addition to the HGF gene introduced in this invention, it is possible to use endogenous cardiac muscle protective factors or regeneration factors against cardiac muscle. For example, it is reported that factors, such as TGF-β and heat shock protein (HSP) expressed highly during damage of the cardiac muscle, reduce myocardiopathy and are engaged in the repair of cardiac muscle. Therefore, it is possible to use the genes encoding them. Moreover, growth factors, such as EGF, are reported to repair cell damage in various tissues and genes encoding them can be also used. In addition to these cardiac muscle protective factors and regeneration factors, factors related to protection and regeneration of the cardiac muscles can be utilized.

According to the invention, it is possible to deliver the protein of interest to damaged cells, such as cardiac muscle cells, by introducing an HGF gene, along or together with other genes, to the cardiac muscle cell of the heart and highly expressing them. This enables activation of repair and regeneration of the damaged cardiac muscle and such, and recuperation of the cardiac function involved in myocardiopathy. Hence, the gene therapy agent of this invention can be applied to patients with critical cardiomyopathy, and offers remedy for patients for whom no options, other than heart transplantation, are left.

Moreover, the therapeutic agent of this invention can be applied not only to patients with severe cardiomyopathy but also to patients with progressive mild cardiomyopathy. It is applicable to patients with a cardiac muscle disorder such as angina pectoris and heart failure as well.

Proper methods and sites for administration adequate for the disease or symptom to be treated are selected for the gene therapy agent of this invention. Cardiac muscle (affected part of the cardiac muscle) is a preferable administration site. As to the administration methods, parenteral administration methods are preferred.

Examples of parenteral administration methods include administration by noninvasive catheter, noninvasive injector and so on. More preferred are administration methods which utilize noninvasive catheter, noninvasive injector and such under the usage of echo. As a method using noninvasive catheter, for example, methods like injecting HGF genes directly can be indicated.

Dosage of the therapeutic agent of this invention varies depending on the symptoms of the patient but HGF genes 0.0001 mg to 100 mg, preferably about 0.001 to 10 mg per adult patients can be defined.

When the HVJ-liposome form is chosen, HGF genes of a range of about 1 to about 4000 μg, preferably about 10 to about 400 μg per adult patient is selected.

The therapeutic agent of this invention is suited for administration once very few days or every few weeks, and administration once per week is preferred.

Frequency of administration is to be selected depending on the symptoms of the patients. In compliance with the object of the treatment, plural administration is suitable, and preferably administration of 8 times can be indicated.

Further to the present invention, a new gene therapy method and therapeutic agent used therefor, including non-invasive administration of therapeutically effective gene for the treatment of the disorder to the affected tissue site under the usage of echo, is presented. That is, it was revealed for the first time that effective treatments can be achieved visually by administering directly the gene to the affected tissue under the usage of echo. According to the therapeutic treatment of the invention, genes are administered noninvasively and therefore desired genes can be administered as much as the condition demands, which is advantageous as compared to former methods. Gene therapy methods of this invention can be applied to any genes, in addition to HGF gene. This gene therapy method of the invention is particularly effective when applied to the affected site of cardiac muscle. Genes administered in such situations include the HGF gene, TGF-β gene, HSP gene, VEGF gene, FGF gene, EGF gene and so on.

The present invention will now be specifically explained with reference to the following examples. It should be noted, however, that the present invention is not limited by these examples in any way.

MATERIALS AND METHODS

Experimental Animals

Hamster model for cardiomyopathy (cardiomyopathy hamster; Bio14.6) was purchased for Oriental Yeast.

HGF Gene

Human HGF gene was cloned from human HGF cDNA (Japanese Patent No. 2777678) according to a conventional method and was inserted into the expression vector pcDNA (Invitrogen).

Experimental Procedure

1. Reporter gene luciferase was introduced into the cardiomyopathy hamster by HVJ liposome under the usage of echo. A week later, the activity of the luciferase was measured. Animals into which PBS was introduced alone under the usage of echo were used as the control. Luciferase activity was measured by a luminometer (LamatLB9507 (BERTHOLO)).

2. Under the usage of echocardiogram (MD500, YOKOKAWA-GE), HVJ-liposome agent was injected into the abdominal lateral cardiac muscle of the heart of myocardiopathy hamster (12 weeks old) and was subjected to following investigations:

1) Density of blood capillary in the cardiac muscle was measured by ALP (alkaline phosphatase) staining and the result of the HGF gene was compared to that of the control.

2) Bloodstream of the heart to which HVJ-liposome was administered was evaluated by laser Doppler imager (LDI) score and the result of the HGF gene was compared to that of the control.

3) After Masson staining of the cardiac muscle, distribution density of fibrosis was measured by computer analysis. Result of the HGF gene was compared to that of the control.

Reference 1

Preparation of HVJ-Liposome Agent 10 mg Dried lipid (a 1:4.8:2 mixture of phosphatidyl serine, phosphatidyl choline and cholesterol) and 200 μl isotonic solution (137 μM NaCl, 5.4 μM KCl, 10 μM Tris-HCl; pH7.6) containing HGF gene (100 μg)-HMG1 (high mobility group 1 nuclear protein, 25 μg) was mixed and, by stirring vigorously with ultrasonication, liopsomes were formed. Purified Sendai virus (Z strain) was irradiated with UV (110 erg/mm$^2$/sec) for 3 minutes. Liposome suspension was mixed with Sendai virus (HVJ), heated at 4° C. for 10 minutes, and then heated at 37° C. for 30 minutes. Free HVJ was discarded and thus obtained HVJ liposome agent.

Reference 2

Measurement on Luciferase Activity

Liposome agent with 10 μg of luciferase gene was administered to hamsters (6 animals per group). A week later, luciferase activity was measured. Results are shown in FIG. 1.

As shown in FIG. 1, high levels of luciferase activity were exhibited in the heart. Thus, it was revealed that gene transfer under the usage of echo is possible.

Experiment 1

Treatment of Myocardiopathy Hamster with HGF Gene

Liposome agent was injected into the abdominal lateral cardiac muscle of the heart of myocardiopathy hamsters (12 weeks old, 6 animals per group). A group of myocardiopathy hamsters (12 weeks old, 6 animals per group) to which liposome agent containing control vectors was injected in the same manner was used as the control and untreated myocardiopathy hamsters (6 animals per group) were used as the untreated group. Then liposome agents were injected once each week for 8 times. 8 weeks later, density of blood capillary in the cardiac muscle of the heart of the 20 week old myocardiopathy hamsters was measured by ALP staining, and bloodflow was evaluated by the LDI score. After euthanization of the hamsters, the heart was extirpated and after Masson staining, distribution density of fibrosis was measured by computer analysis.

Figure 2:
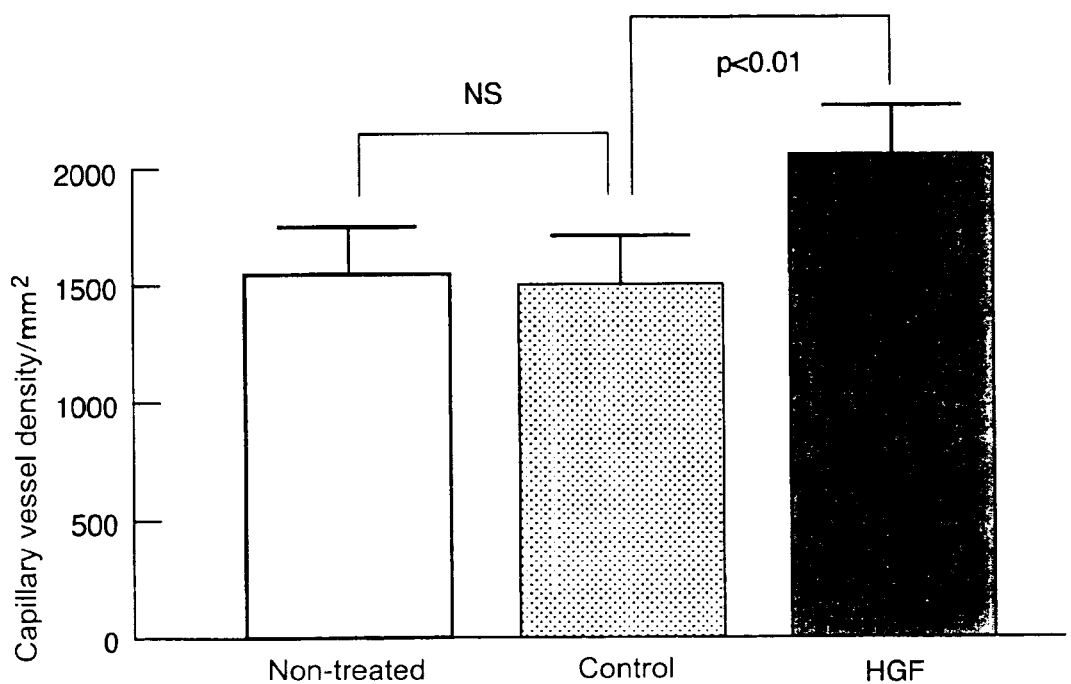
FIG. 2 is a graph showing the result of a comparison between an HGF gene and a control by measuring cardiac capillary vessel density by ALP (alkaline phosphatase) staining.

ALP staining revealed significant rise in blood capillary by angiogenesis in HGF gene treatment group. The results are shown in FIG. 2.

Figure 3:
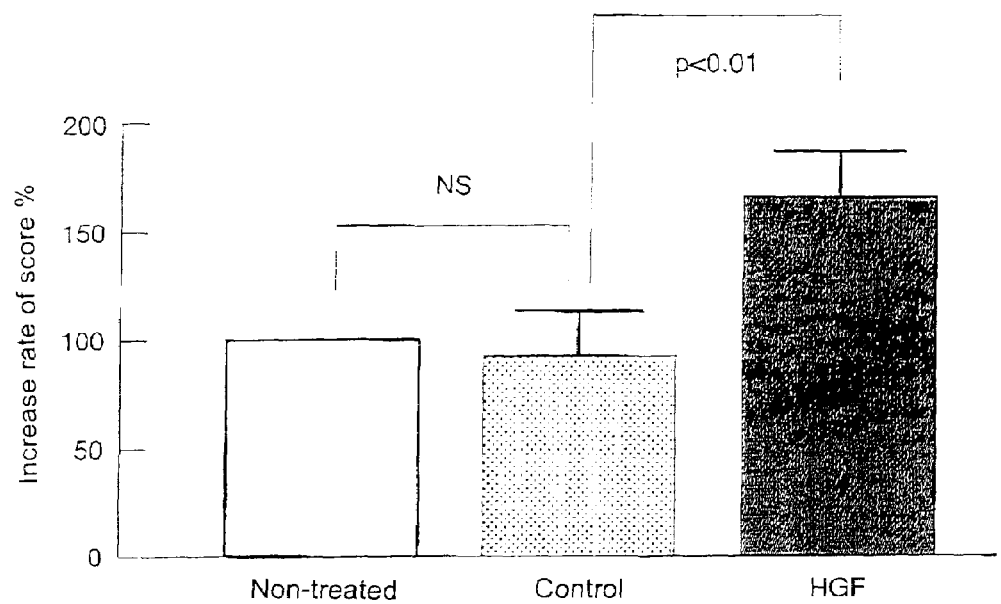
FIG. 3 is a graph showing the result of a comparison of the amount of cardiac bloodstream between an HGF gene group, a control group and a non-treated group by evaluation with a laser Doppler imager (LDI).

Concerning LDI score, taking the control group as 100%, the HGF gene treatment group was 163±7%, which indicates significant increase in bloodflow. The results are shown in FIG. 3.

Figure 4:
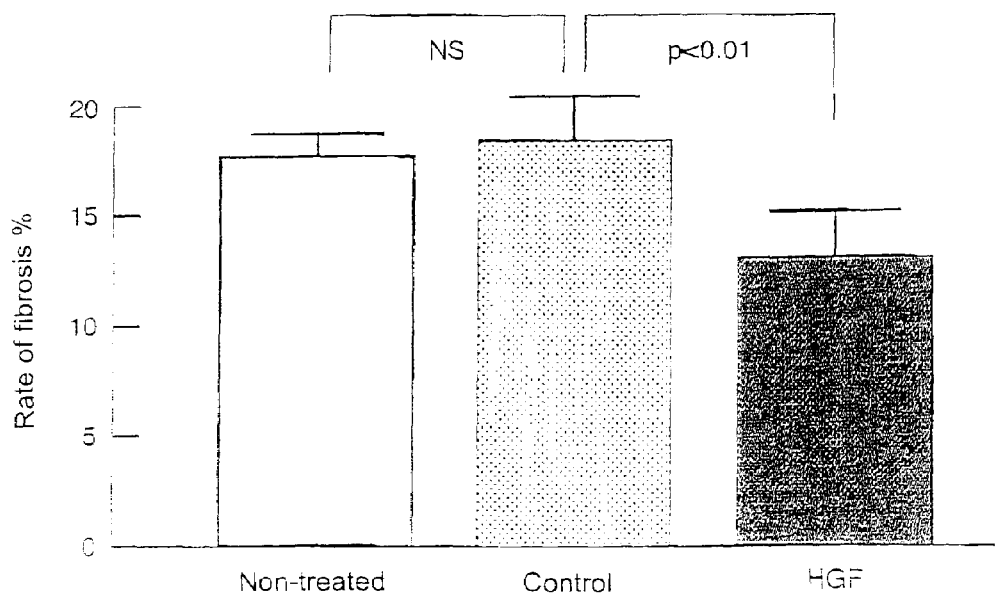
FIG. 4 is a graph showing the result of a comparison of the distribution density of fibrosis of the heart by measurement using Masson staining.

According to the analysis of Masson staining, significant decrease in distribution density of fibrosis was observed in HGF gene treatment group. The results are shown in FIG. 4.

INDUSTRIAL APPLICABILITY

Therapeutic agents for myocardiopathy comprising an HGF gene of this invention induce angiogenesis of the affected part of cardiac muscle, increase bloodflow of the affected part while repressing and reducing fibrosis of the cardiac muscle it can repair the cardiac function. Moreover, therapeutic agents of this invention can be injected noninvasively and accurately to the affected cardiac muscle layer visually under the usage of echo. Therefore, therapeutic agents of the invention enable more effective treatment of myocardiopathy.

We claim:

1. A method for treating a cardiac muscle disorder comprising administering a therapeutically effective amount of a nucleic acid molecule encoding hepatocyte growth factor (HGF) directly to a part of an affected abdominal lateral cardiac muscle of a mammal using echocardiographic guidance without thoracotomy, wherein the nucleic acid molecule is encapsulated in a Sendai virus (HVJ)-liposome and expresses an HGF protein that reduces fibrosis and/or promotes angiogenesis of the cardiac muscle, thereby treating the cardiac muscle disorder.

2. A method for treating a cardiac muscle disorder comprising administering a therapeutically effective amount of a nucleic acid molecule encoding HGF directly into an abdominal lateral cardiac muscle of a mammal, wherein the nucleic acid molecule is administered once a week for 8 weeks, wherein the nucleic acid molecule is encapsulated in a Sendai virus (HVJ)-liposome and expresses and HGF protein that reduces fibrosis and/or promotes angiogenesis of the cardiac muscle, thereby treating the cardiac muscle disorder.

3. The method of claim 1, wherein the cardiac muscle disorder is angina pectoris or heart failure.

4. A method for treating a cardiac muscle disorder comprising administering a therapeutically effective amount of a nucleic acid molecule encoding HGF directly into a abdominal lateral cardiac muscle of a mammal, wherein administering comprises administering the nucleic acid molecule under echocardiographic guidance without thoracotomy through a catheter, wherein the nucleic acid molecule is encapsulated in a Sendai virus (HVJ)-liposome and expressions an HGF protein that reduces fibrosis and/or promotes angiogenesis of the cardiac muscle, thereby treating the cardiac muscle disorder.

* * * * *

UNITED STATES PATENT AND TRADEMARK OFFICE
CERTIFICATE OF CORRECTION

| | |
|---|---|
| PATENT NO. | : 6,989,374 B1 |
| APPLICATION NO. | : 09/857719 |
| DATED | : January 24, 2006 |
| INVENTOR(S) | : Morishita et al. |

It is certified that error appears in the above-identified patent and that said Letters Patent is hereby corrected as shown below:

On the Title Page of Patent, page 1:

Column 2, line 6, insert --Aoki, et al., "Efficient *in vivo* Gene Transfer into the Heart in the Rat Myocardial Infarction Model Using the HVJ (Hemagglutinating Virus of Japan)--Liposome Method," *J. Mol. Cell. Cardiol.* 29:949-959 (1997)--

Column 2, line 28, "Transfer of Vascular Growth" should read --Transfer of Endothelial Vascular Growth--.

Column 2, line 43, "Arterial Gene Therapy For Therapy For" should read --Arterial Gene Therapy For--.

On the Title Page of Patent, page 2:

Column 1, lines 14-15, "The Basic Science of Gene Therapy, " should read --"The Basic Science of Gene Therapy,"--.

Column 1, line 55, "In the Coronary," Circulation 88(4): 2561 (1993)" should read --In the Coronary Circulation," *Circulation* 88(4) 2561 (1993)--.

In the Claims:

Column 8, line 64, "directly to a part" should read --directly into a part--.

Column 9, line 10, "(HVJ)-liposome and expresses and HGF protein" should read --(HVJ)-liposome and expresses an HGF protein--.

UNITED STATES PATENT AND TRADEMARK OFFICE
CERTIFICATE OF CORRECTION

PATENT NO. : 6,989,374 B1
APPLICATION NO. : 09/857719
DATED : January 24, 2006
INVENTOR(S) : Morishita et al.

It is certified that error appears in the above-identified patent and that said Letters Patent is hereby corrected as shown below:

In the Claims (cont'd):

Column 10, lines 9-10, "and expressions" should read --and expresses--.

Signed and Sealed this

Twenty-eighth Day of August, 2007

JON W. DUDAS
*Director of the United States Patent and Trademark Office*